United States Patent [19]

Wall

[11] Patent Number: 5,577,841
[45] Date of Patent: Nov. 26, 1996

[54] MOLTEN METAL IMMERSION PROBE

[75] Inventor: Christopher Wall, Bridgewater, N.J.

[73] Assignee: Heraeus Electro-Nite International N.V., Antwerp, Belgium

[21] Appl. No.: 384,985

[22] Filed: Feb. 6, 1995

[51] Int. Cl.⁶ .................................................. G01N 1/12
[52] U.S. Cl. ...................... 374/140; 374/157; 73/DIG. 9; 136/234
[58] Field of Search ..................... 374/139, 140, 374/157, 166, 179, 181, 208; 73/864.51, 864.53, DIG. 9; 136/234

[56] References Cited

U.S. PATENT DOCUMENTS

| | | | |
|---|---|---|---|
| 3,456,164 | 7/1969 | Sternberg | 317/148.5 |
| 3,463,005 | 8/1969 | Hance | 374/140 |
| 3,577,886 | 5/1971 | Wiese | 374/139 |
| 3,656,346 | 4/1972 | Collins | 374/140 |
| 3,656,347 | 4/1972 | Collins | 374/140 |
| 3,709,040 | 1/1973 | Coe | 374/140 |
| 3,915,002 | 10/1975 | Hance et al. | 374/140 |
| 3,922,916 | 12/1975 | Wickert | 374/140 |
| 3,950,992 | 4/1976 | Hance | 374/140 |
| 4,007,641 | 2/1977 | Kelsey | 73/DIG. 9 |
| 4,361,053 | 11/1982 | Jones et al. | 73/864.53 |
| 4,401,389 | 8/1983 | Theuwis | 374/140 |
| 4,778,281 | 10/1988 | Falk | 374/140 |
| 4,842,418 | 6/1989 | Conti | 73/DIG. 9 |

FOREIGN PATENT DOCUMENTS 0095102  11/1983  European Pat. Off. .

Primary Examiner—G. Bradley Bennett
Attorney, Agent, or Firm—Panitch Schwarze Jacobs & Nadel, P.C.

[57] ABSTRACT

An immersion probe for determining a liquidus temperature of a molten metal sample during solidification has a first refractory body with an immersion face, an interior sample chamber, and a passageway between the immersion face and an end wall of the chamber. A heat sink is positioned within the chamber adjacent the end wall and an insulating shield is positioned within the chamber adjacent the heat sink, each having an aperture corresponding to the inlet tube. The insulating shield sinks thermal energy from within the chamber at a second rate $R_2$ slower than a first rate $R_1$ of the interior walls of the chamber. A liquidus temperature sensor is positioned within the chamber away from the insulating shield. To determine the liquidus temperature, the probe is immersed in the molten metal, and a molten metal sample flows into the chamber through the passageway. When the flow ceases, the heat sink solidifies an adjacent portion of the molten metal and seals the sample within the chamber. The sealed sample solidifies along a solidification front that progresses toward the insulating shield. Accordingly, gaseous voids are prevented from being formed adjacent the sensor while the liquidus temperature is determined.

19 Claims, 2 Drawing Sheets

MOLTEN METAL IMMERSION PROBE

FIELD OF THE INVENTION

The present invention relates generally to immersion sensors for use in molten metal processing vessels which can obtain the liquidus temperature of the molten metal during solidification. More particularly, the present invention relates to a molten metal immersion probe that obtains a molten metal sample and that solidifies the sample in a particular manner to more reliably measure liquidus temperature information.

BACKGROUND OF THE INVENTION

A common sampling technique for determining the chemical analysis of molten metal utilizes a measurement of the temperature at which the molten metal solidifies. Accordingly, a sampling device having an internal cavity and a temperature sensing element positioned within the cavity is immersed into a bath of the molten metal, the molten metal enters the cavity through an inlet, and the cavity fills under the force of ferrostatic pressure. In typical prior art sampling devices, the molten metal sample solidifies along a solidification front that progresses from the walls of the cavity toward the thermal and geometric center of the cavity.

As is known, during solidification, gases in the molten metal become segregated along the solidification front and may accumulate to form gas voids in the last metal to freeze, i.e. near the thermal center of the cavity. A problem arises with typical prior art sampling devices, however, in that the temperature sensing element is generally positioned at or near the center of the filled cavity and the adjacent gas voids interfere in the heat transfer from the solidifying metal to the sensing element. The interfered heat transfer results in inaccurate and inconsistent temperature sensing measurements. A need exists, then, for a sampling device that controls molten metal solidification to prevent gas voids from being formed at or near the temperature sensing element.

Another problem with a typical prior art sampling device is that the reliability of the device is dependent upon the ability of the internal cavity to fill completely when the device is immersed within the molten metal bath and to remain filled when the device is withdrawn from the molten metal bath. As may be understood, void formation near the temperature sensing element can also occur when a portion of the molten metal sample within the cavity escapes and/or when the cavity does not completely fill with the molten metal. A need exists, then, for a sampling device having an internal cavity that substantially completely fills when the sampling device is immersed within the bath and that remains substantially completely filled when the sampling device is removed from the bath.

In prior art sampling devices, it is also known to have two separate temperature sensors, one for measuring the liquidus temperature at which the molten metal solidifies and one for measuring the ambient bath temperature of the molten metal bath. In the case where the temperature sensing devices are thermocouples, it is necessary to maintain a constant temperature for the junctions of the thermocouples and their respective compensated lead wires. However, still another problem with a typical prior art sampling device is that latent heat given off by the solidifying metal in the internal cavity can affect such junctions and compensated lead wires and may result in inaccurate temperature readings. A need exists, then, for a sampling device that shields such junctions and lead wires from such latent heat.

SUMMARY OF THE INVENTION

The aforementioned needs are satisfied by an immersion probe for collecting a sample of the molten metal and for determining a liquidus temperature of the metal during solidification. Briefly stated, the probe is generally longitudinally shaped and is immersed in the molten metal in an immersion direction, with a first longitudinal end of the probe initially contacting the molten metal. The probe has a first refractory body with an immersion face facing toward the first end of the probe, an interior sample chamber, and a passageway extending between the immersion face and the sample chamber. Importantly, the interior walls of the sample chamber sink thermal energy from within the sample chamber at a first rate $R_1$.

A heat sink is positioned within the sample chamber adjacent a first end wall proximate the immersion face, and the heat sink has an aperture through which molten metal passes from the passageway into the sample chamber. An insulating shield is positioned within the sample chamber adjacent the heat sink such that the heat sink is insulated from thermal energy within the sample chamber, and the insulating shield has an aperture through which the molten metal flows after the molten metal passes through the heat sink aperture. Importantly, the insulating shield sinks thermal energy from adjacent molten metal at a second rate $R_2$ slower than the first rate $R_1$. A liquidus temperature sensor is positioned within the sample chamber away from the insulating shield.

In a method for collecting a sample of a molten metal and for determining from the sample a liquidus temperature of the molten metal during solidification that employs the afore-described immersion probe, the probe is immersed in the molten metal and the molten metal flows into the sample chamber through the passageway until the sample chamber is substantially filled. When the flow of the molten metal ceases, the heat sink sinks thermal energy from and solidifies adjacent molten metal. The solidified molten metal seals the sample within the sample chamber, and the sealed sample solidifies along a solidification front that progresses toward the insulating shield. With the solidification front directed as such, gaseous voids are prevented from being formed adjacent the liquidus temperature sensor, and the liquidus temperature of the molten metal during solidification is determined from the solidifying sample with the liquidus temperature sensor.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF PREFERRED EMBODIMENTS

Figure 1:
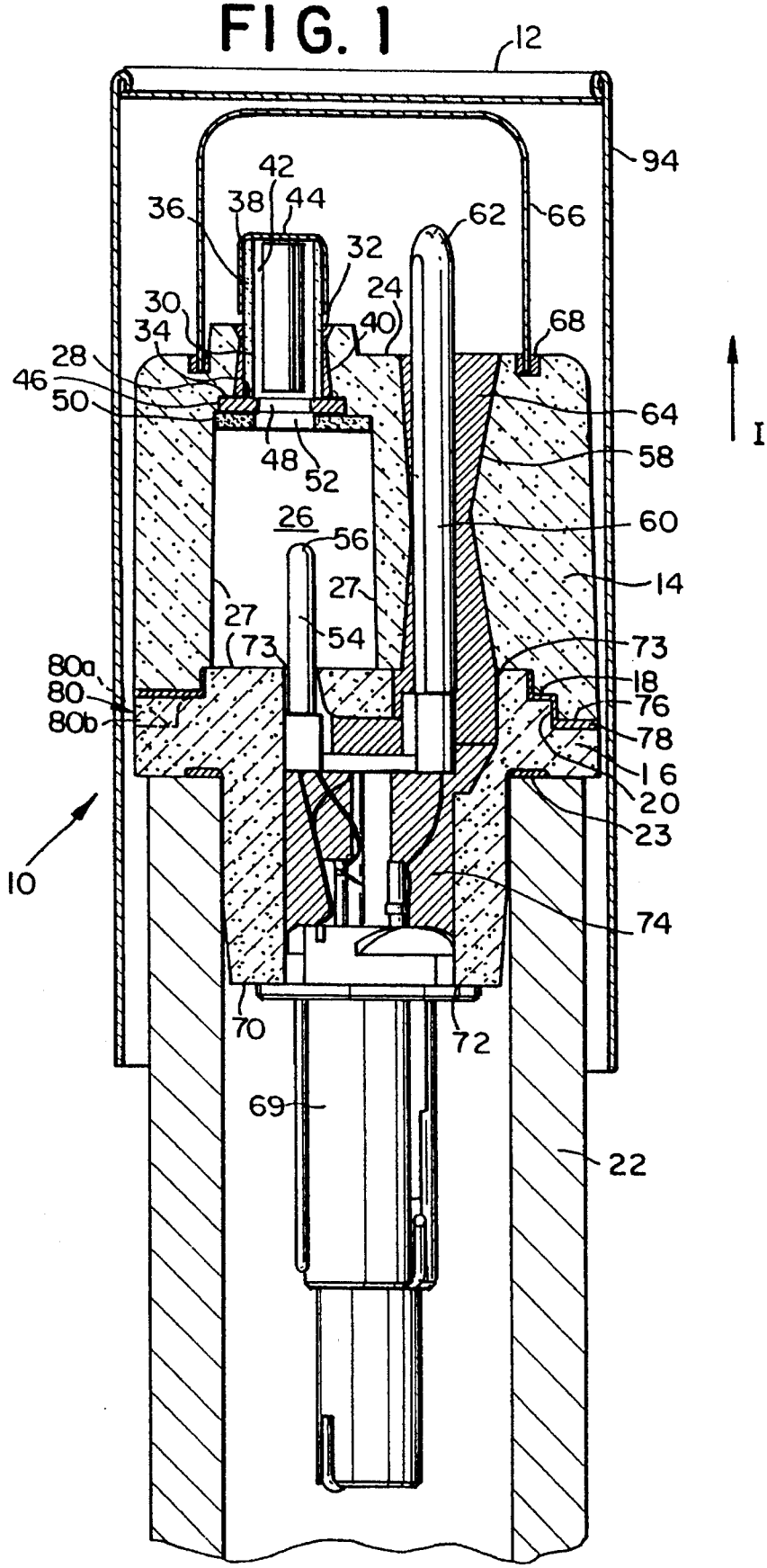
FIG. 1 is an elevational cross-sectional view of a molten metal immersion probe constructed in accordance with a preferred embodiment of the present invention.

Certain terminology may be used in the following description for convenience only and is not limiting. The words "left", "right", "upper" and "lower" designate directions in the drawings to which reference is made. The words "inwardly" and "outwardly" are further directions toward and away from, respectively, the geometric center of a referenced object. The terminology includes the words above specifically mentioned, derivatives thereof, and words of similar import.

Referring to the drawings in detail wherein like numerals are used to indicate like elements throughout, there is shown in FIG. 1 a molten metal immersion probe 10 for collecting a sample of a molten metal and for determining a liquidus temperature of the metal during solidification, in accordance with the present invention. The probe 10 is generally longitudinally shaped and is immersed in the molten metal (not shown) in an immersion direction I. As such, the probe 10 initially contacts the molten metal at a first longitudinal end 12. The probe 10 has first and second generally porous refractory bodies 14, 16 bonded together at respective first and second abutting faces 18, 20, and is positioned at one end of a consumable cardboard tube 22. The tube 22 may be interference fitted to the probe 10 at the second body 16, as seen in FIG. 1, and an adhesive agent 23 may also be employed to secure the tube 22 to the second body 16.

The first body 14 has an immersion face 24 facing generally toward the first end 12 of the probe 10 and generally opposite the first abutting face 18. Within the first body 14 is an interior sample chamber 26 defined by a plurality of interior walls 27 including a first end wall 28 proximate to and generally parallel with respect to the immersion face 24. The material surrounding the sample chamber 26 and forming the interior walls 27 sinks thermal energy from within the sample chamber 26 at a first rate $R_1$ and solidifies a molten metal sample (not shown) in the sample chamber 26 at a desired rate for thermal analysis.

Preferably, the size and geometry of the sample chamber 26 allow the collection of a large-enough molten metal sample for a proper liquidus temperature determination. Also preferably, one of the interior walls 27 of the sample chamber 26 has a large, flat surface area to produce a like flat surface area on the solidified molten metal sample. As may be realized, such a flat surface area aids in the preparation of the solidified sample for spectrometer analysis.

Preferably, the first and second bodies 14, 16 are constructed from a porous refractory material, such as baked resin sand, to allow air to ventilate from the sample chamber 26 when the chamber 26 is filled with the molten metal sample. Also, it is preferable that the material surrounding the sample chamber 26 is thick enough to provide the necessary mechanical strength and to thermally shield or insulate the solidifying sample within the sample chamber 26 from thermal energy from the molten metal bath (not shown).

The first body 14 has a passageway 30 extending between an opening 32 in the immersion face 24 and a portal 34 in the first end wall 28, and, in the present embodiment, an inlet tube 36 extends through the passageway 30 and past the immersion face 24 generally in the immersion direction I to an external end 38. Preferably, the inlet tube 36 is constructed from quartz and is fixed in place with a refractory cement 40. However, the inlet tube 36 may also be constructed from another material such as ceramic or metal and may be fixed in place with other fixing agents without departing from the spirit and scope of the present invention. Alternatively the tube 36 may be eliminated such that molten metal flows directly through the passageway 30.

Within the inlet tube 36 is a deoxidant, in the present embodiment a deoxidizing liner 42 that extends along at least a portion of the inlet tube 36 and preferably along the entire length of the tube 36. As should be understood, the deoxidizing liner 42 deoxidizes the sample of molten metal as it enters the sample chamber 26 through the inlet tube 36. Preferably, the deoxidizing liner is an aluminum liner, although one skilled in the art will recognize that other deoxidizing materials and geometries (i.e. wires, meshes, strips, etc.) may be employed without departing from the spirit and scope of the present invention.

The probe 10, in the present embodiment, has a first metal cap 44 covering the external end 38 of the inlet tube 36 to prevent materials from prematurely entering the sample chamber 26. As should be understood, then, the first cap 44 is constructed of a metal material that dissolves upon contact with the molten metal for a predetermined time period. If desired, the first metal cap 44 may be eliminated for some applications.

Within the sample chamber 26 and adjacent the first end wall 28 is a heat sink 46 having an aperture 48 corresponding in size with and generally aligned with the portal 34 in the first end wall 28 through which the molten metal passes from the inlet tube 36 and into the sample chamber 26. Preferably, the heat sink 46 is a circular steel washer. However, a high heat capacity metal such as copper or ceramic such as alumina nitrate may be employed without departing from the spirit and scope of the present invention.

Covering the heat sink 46 within the sample chamber 26 is an adjacent insulating shield 50. The shield 50 has an aperture 52 corresponding in size with and generally aligned with the aperture 48 in the heat sink 46 and the portal 34 in the first end wall 28. Importantly, the insulating shield 50 sinks thermal energy from within the sample chamber 26 at a second rate $R_2$ which is slower than the first rate $R_1$ of the interior walls 27. Accordingly, it is preferable that the insulating shield 50 be constructed from a highly insulating fibrous refractory material. Preferably, the insulating shield 50 is press fit within the sample chamber 26 and secures the heat sink 46 in place.

With the insulating shield 50 covering the heat sink 46, the mass of molten metal within the sample chamber 26 is thermally separated from the heat sink 46. The heat sink 46 is thereby protected from thermal energy from molten metal within the sample chamber 26. Accordingly, the heat sink 46 can only absorb thermal energy from molten metal at and about the aperture 48 extending therethrough. As a result, when the probe 10 is immersed within the molten metal bath and the sample chamber 26 becomes filled with the molten metal sample, the flow of molten metal into the chamber stops and the portion of the molten metal in contact with the heat sink 46 at the aperture 48 quickly solidifies to entrap and seal the molten metal sample within the sample chamber 26.

Since the insulating shield 50 sinks thermal energy from within the sample chamber 26 at a second rate $R_2$ slower than the first rate $R_1$ of the interior walls 27 of the sample chamber, the thermal center of the sample chamber 26 is moved away from the geometric center of the sample chamber 26 and toward the immersion face 24 of the first body 14, and the molten metal sample sealed within the sample chamber 26 solidifies along a solidification front that progresses toward the insulating shield 50. Accordingly, the last metal to begin freezing and the metal most likely to have gaseous voids is formed adjacent the insulating shield 50.

The probe 10 has a liquidus temperature sensing device 54 that extends through an opening in the first abutting face 18 of the first body 14 and into the sample chamber 26 to a sensor 56 at a sensing end. The sensor 56 is positioned within the sample chamber 26 away from the insulating shield 50 and thus away from the thermal center of the sample chamber 26. Accordingly, gaseous voids are prevented from being formed adjacent the sensor 56. Preferably, the sensor 56 is positioned at or about the geometric center of the sample chamber 26, although it will be recognized that the sensor 56 may also be positioned at other locations away from the insulating shield 50 without departing from the spirit and scope of the present invention.

Preferably, the probe 10 is employed to concurrently determine a bath temperature of the molten metal and the liquidus temperature of the molten metal during solidification. Consequently, the first body 14 has a generally longitudinal channel 58 extending between the immersion face 24 and the first abutting face 18, and a bath temperature sensing device 60 extends through the longitudinal channel 58 and past the immersion face 24 to a bath sensor 62 at a sensing end. Preferably, the remaining space in the longitudinal channel 58 is filled with an insulating filler material 64 to secure the bath temperature sensing device 60 to the first body 14. The material 64 is preferably a refractory material such as resin-coated sand or refractory cement, although one skilled in the art will recognize that other similar materials may be employed without departing from the spirit and scope of the present invention. As should be understood, the material 64 provides the necessary insulation from the thermal energy released from the solidifying molten metal sample in the sample chamber 26, as well as from the surrounding molten metal bath.

Preferably, the first body 14 also has a second metal cap 66 positioned at the first longitudinal end 12 of the probe 10 to protect the first cap 44 and the sensor 62 of the bath temperature sensing device 60 prior to and during immersing of the probe 10 within the molten metal bath. To accommodate the second cap 66, it is preferable that the immersion face 24 of the first body 14 have a groove 68 into which the edge of the second cap 66 is mounted. The second cap 66 may be secured in the groove 68 by a bonding cement or other securing agents which should be apparent to one skilled in the art. When the probe 10 is immersed within the molten metal bath, the second metal cap 66 dissolves upon contact with the molten metal for a predetermined time period and the sensor 62 of the bath temperature sensing device 60 and the first metal cap 44 become exposed to the molten metal in the bath.

Preferably, and as seen in FIG. 1, the second refractory body 16 is fitted to the first refractory body 14 by way of the respective first and second abutting faces 18, 20 such that a portion of the second abutting face 20 forms one of the interior walls 27 of the sample chamber 26. Also preferably, the second body 16 has a connector face 70 generally opposite the second abutting face 20, and an electrical connector 69 extends into the second body 16 from the connector face 70. As seen in FIG. 1, the electrical connector 69 supports the liquidus temperature sensing device 54 and the bath temperature sensing device 60, and the sensing devices 54, 60 are electrically connected to and extend from the electrical connector 69 to the respective sensors 56, 62.

The electrical connector 69 is constructed from a non-conductive material such as plastic, and is press fit into the second body 16 at an aperture 72 in the connector face 70. Preferably, the second body 16 has openings 73 at the second abutting face 20 through which the sensing devices 54, 60 extend, and the second body 16 is shaped to allow only one possible orientation for mounting the electrical connector 69 and the sensing devices 54, 60 to the second body 16. Preferably, a refractory cement 74 is employed to secure the electrical connector 69 and the sensing devices 54, 60 to the second body 16.

Preferably, the first and second abutting faces 18 and 20 of the respective first and second bodies 14, 16 each have a radial step configuration 76 such that the first abutting face 18 is complementarily received by the second abutting face 20. With the radial step configuration 76, the bonding surface area between the first and second bodies 14, 16 is maximized to assure a strong bond by way of a bonding agent 78. Preferably, the bonding agent 78 is a refractory cement, although one skilled in the art will recognize that other bonding materials may be employed without departing from the spirit and scope of the present invention.

The first and second abutting faces 18, 20 preferably also have a tongue and groove arrangement 80 to prevent the first and second bodies 14, 16 from rotating with respective to each other. As seen in FIG. 1, the tongue 80a extends from the first body 14 and is received by a groove 80b in the second body 16. Of course, it will be recognized that the respective positions of the tongue and groove 80, 82 may be reversed or other means for preventing rotation of the first and second bodies 14, 16 may be employed without departing from the spirit and scope of the present invention.

Figure 2:
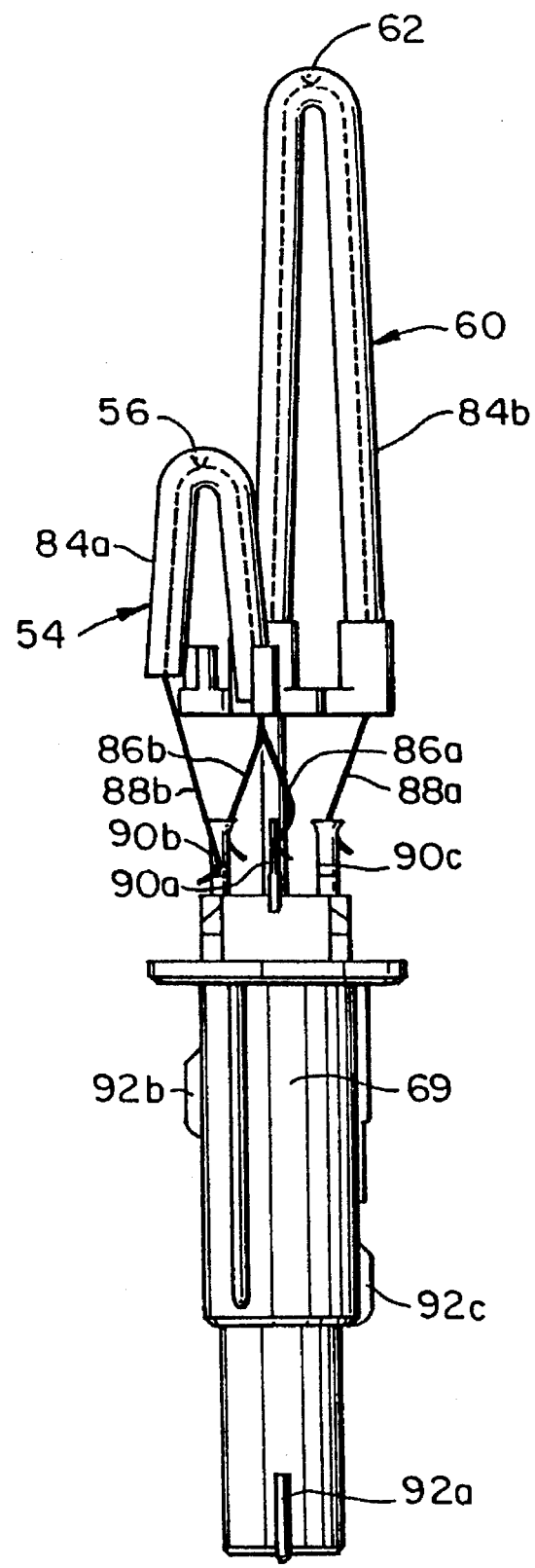
FIG. 2 is an elevational perspective view of the thermocouples and the electrical connector of the probe shown in FIG. 1.

Referring now to FIG. 2, the sensing devices 54, 60 will be discussed in more detail. Preferably, both sensing devices 54, 60 are thermocouples having noble bi-metal thermoelements such as platinum/platinum-rhodium (not shown). However, one skilled in the art will recognize that other types of thermoelements and thermocouples may be employed without departing from the spirit and scope of the present invention.

The sensors 56, 62 of the respective thermocouples 54, 60 are protected with thin wall quartz tubes 84a, 84b, as is well known in the expendable thermocouple art, and conductive wires 86a, 86b, 88a, 88b respectively extend from the sensors 56, 62 to the electrical connector 69. Preferably, the wires 86a, 86b, 88a, 88b are connected to the electrical connector 69 at compensated junctions 90a, 90b, 90c. As seen in FIG. 2, wire 86a is connected to junction 90a, wires 86b and 88b are connected to junction 90b, and wire 88a is connected to junction 90c. Preferably, the compensated junctions 90a, 90b, 90c are located at the same general longitudinal position within the refractory cement 74 of the second body 16. Accordingly, the compensated junctions 90a, 90b, 90c are in thermal equilibrium and unwanted thermoelectric forces are prevented. Preferably, the compensated junctions 90a, 90b, 90c are respectively electrically connected to compensated contacts 92a, 92b, 92c and a temperature recording device (not shown) is electrically connected to the probe 10 at the contacts 92a, 92b, 92c when the probe 10 is in use.

As should be understood, a molten metal bath typically has a slag layer (not shown) at the uppermost region of the bath where the molten metal is exposed to air and is partially solidified. Accordingly, once all the aforementioned elements are assembled to form the probe 10, it is preferable that a paper cap 94 (as seen in FIG. 1) be placed over the probe 10 to protect the probe 10 and especially the first end 12 of the probe 10 when initially inserted through the slag layer during immersion. The paper cap 94 is consumed during the transit through the slag layer, but slag is prevented from freezing to the second metal cap 66 during passage of the probe 10 to the molten metal below the slag layer.

With the probe 10 as described above, a method for collecting a sample of a molten metal and for determining from the sample a liquidus temperature of the molten metal during solidification and also for concurrently determining a bath temperature of the molten metal will be described. Preliminarily, the probe 10 is suspended by the cardboard tube 22 from a metal pole (note shown) that has a non-directional mating end in electrical contact with the electrical connector 69. The probe 10 is then immersed into a molten metal bath, through the slag layer atop the molten metal, and into the molten metal itself. The paper cap 94 is consumed while the probe 10 crosses the slag layer, but the second metal cap 66, the bath sensor 62 and the inlet tube 36 are protected from the slag.

Once the probe 10 enters the molten metal, the molten metal contacts and dissolves the second cap 66, exposing the first cap 44 and the bath temperature sensing device 60 to the molten metal. Accordingly, the bath sensor 62 begins to determine the bath temperature of the molten metal almost instantly, and the molten metal contacts and dissolves the first cap 44 to open the inlet tube 36. As a result, a sample of the molten metal flows into the sample chamber 26 through the inlet tube 36 under ferrostatic pressure until the sample chamber 26 is filled. While the sample of the molten metal is flowing through the inlet tube 36, the sample is deoxidized by the deoxidizing liner 42. As should be understood, air in the sample chamber 26 is evacuated during the filling operation through the porous first and second refractory bodies 14, 16.

Once the chamber 26 is substantially filled with the sample of the molten metal, the flow through the inlet tube 36 ceases, and the heat sink 46 sinks thermal energy from a portion of the molten metal adjacent the aperture 48 of the heat sink 46 to solidify the portion. Accordingly, the solidified portion of the metal proximate the heat sink 46 seals the molten metal sample within the sample chamber 26, and the liquidus sensor 56 located within the sample chamber 26 begins to determine the temperature of the molten metal sealed within the sample chamber 26. Since the insulating shield 50 sinks thermal energy from within the sample chamber 26 at a second rate $R_2$ slower than the first rate $R_1$ of the interior walls 27 of the sample chamber 26, the thermal center of the sample chamber 26 is moved away from the liquidus sensor 56, the sealed sample solidifies along a solidification front that progresses toward the insulating shield 50, and gaseous voids are prevented from being formed adjacent the liquidus sensor 56 during solidification.

As the solidification front passes the liquidus sensor 56, the latent heat released during solidification balances the heat removal through the interior walls 27 of the sample chamber 26 and a characteristic liquidus arrest temperature may be measured with the liquidus sensor 56. Accordingly, with the temperature readings provided by the liquidus sensor 56 during solidification, a cooling curve analysis during solidification may be performed to determine a chemical analysis of the molten metal. Thereafter, the probe 10 may be removed from the molten metal bath and the solidified sample within the sample chamber 26 may be removed for further analysis.

From the foregoing description, it can be seen that the present invention comprises a new and useful molten metal immersion sensor that prevents gaseous voids from being formed in a sample chamber 26 adjacent the liquidus sensor 56, that insures that the sample chamber 26 fills completely and remains filled, even during removal from the molten metal bath and that prevents non-uniform heating of the compensated connections for the liquidus and bath sensing devices 54, 60. It will be appreciated by those skilled in the art that changes could be made to the embodiment described above without departing from the broad inventive concepts thereof. It is understood, therefore, that this invention is not limited to the particular embodiment disclosed, but it is intended to cover modifications within the spirit and scope of the present invention as defined by the appended claims.

I claim:

1. An immersion probe for collecting a sample of a molten metal and for determining a liquidus temperature of the molten metal during solidification, the probe being generally longitudinally shaped and being immersed in the molten metal in an immersion direction, the probe initially contacting the molten metal at a first longitudinal end, the probe comprising:

a first refractory body having an immersion face facing generally toward the first end of the probe, an interior sample chamber defined by a plurality of interior walls including a first end wall proximate the immersion face, and a passageway extending between an opening in the immersion face and a portal in the first end wall, the interior walls sinking thermal energy from within the sample chamber at a first rate $R_1$;

a heat sink positioned within the sample chamber adjacent the first end wall, the heat sink having an aperture therethrough corresponding to the portal in the first end wall;

an insulating shield within the sample chamber adjacent the heat sink, the insulating shield having an aperture therethrough corresponding to the aperture in the heat sink and the portal in the first end wall, the insulating shield sinking thermal energy from within the sample chamber at a second rate $R_2$ slower than the first rate $R_1$; and a liquidus temperature sensor positioned within the sample chamber away from the insulating shield, wherein when the probe is immersed in the molten metal, molten metal flows into the sample chamber through the passageway until the sample chamber is substantially filled, the heat sink sinks thermal energy from and solidifies a portion of the molten metal proximate thereto when the flow ceases, the solidified portion seals the sample within the sample chamber, the sealed sample solidifies along a solidification front that progresses toward the insulating shield, gaseous voids are prevented from being formed adjacent the liquidus temperature sensor, and the liquidus temperature of the molten metal during solidification is determined from the solidifying sample with the liquidus temperature sensor.

2. The probe of claim 1 further comprising a deoxidant within at least a portion of the passageway for deoxidizing the molten metal flowing through the passageway.

3. The probe of claim 1 for concurrently determining a bath temperature of the molten metal and the liquidus temperature of the molten metal during solidification, the probe further comprising a bath temperature sensor positioned beyond the immersion face.

4. The probe of claim 3 wherein the first body further has a generally longitudinal channel extending therethrough, the probe further comprising a bath temperature sensing device extending through the longitudinal channel and past the immersion face to the bath temperature sensor.

5. The probe of claim 4 further comprising an insulating filler material filling the longitudinal channel around the bath temperature sensing device and securing the bath temperature sensing device to the first body.

6. The probe of claim 3 further comprising a metal cap positioned at the first end, the cap covering the bath temperature sensor, wherein the cap dissolves upon contact with the molten metal when the probe is immersed therein.

7. The probe of claim 3 wherein the first body further has a first abutting face facing generally opposite the first end of the probe and wherein the probe further comprises a second refractory body having a second abutting face abutting the first abutting face of the first body and a connector face generally opposite the second abutting face, the first and second bodies being bonded together at the first and second abutting faces, a portion of the second abutting face forming a second end wall of the sample chamber.

8. The probe of claim 7 further comprising an electrical connector extending into the second body from the connector face, a liquidus temperature sensing device electrically connected to and extending from the electrical connector through the first and second abutting faces to the liquidus temperature sensor, and a bath temperature sensing device electrically connected to and extending from the electrical connector through the first and second abutting faces to the bath temperature sensor.

9. The probe of claim 7 further comprising refractory cement securing the liquidus temperature sensing device, the bath temperature sensing device, and the electrical connector to the second body.

10. The probe of claim 7 wherein the first and second abutting faces each have a radial step configuration, the first abutting face being complementarily received by the second abutting face.

11. The probe of claim 10 wherein one of the first and second abutting faces further comprises a tongue projecting toward the other of the first and second abutting faces and the other abutting face further comprises a groove complementarily receiving the tongue.

12. The probe of claim 1 further including an inlet tube extending through the passageway and past the immersion face generally in the immersion direction to an external end.

13. The probe of claim 12 further including a metal cap covering the external end of the inlet tube, the cap being dissolvable upon contact with the molten metal.

14. The probe of claim 12 further comprising a deoxidizing liner extending along at least a portion of the inlet tube for deoxidizing molten metal flowing through the inlet tube.

15. The probe of claim 3 wherein the liquidus temperature sensor comprises a first thermocouple and the bath temperature sensor comprises a second thermocouple, each of the thermocouples having a pair of wires extending therefrom, and wherein the probe further comprises an electrical connector, the thermocouple wires being connected to the electrical connector at a plurality of compensating junctions, each of the junctions being located at the same general longitudinal position within the probe such that all the junctions are in thermal equilibrium.

16. A method for collecting a sample of a molten metal and for determining from the sample a liquidus temperature of the molten metal during solidification, the method employing a molten metal immersion probe having a generally longitudinal shape and being immersed in the molten metal in an immersion direction, the probe initially contacting the molten metal at a first longitudinal end, the probe comprising:

a first refractory body having an immersion face facing generally toward the first end of the probe, an interior sample chamber defined by a plurality of interior walls including a first end wall proximate the immersion face, and a passageway extending between an opening in the immersion face and a portal in the first end wall, the interior walls sinking thermal energy from within the sample chamber at a first rate $R_1$;

a heat sink positioned within the sample chamber adjacent the first end wall, the heat sink having an aperture therethrough corresponding to the portal in the first end wall;

an insulating shield within the sample chamber adjacent the heat sink, the insulating shield having an aperture therethrough corresponding to the aperture in the heat sink and the portal in the first end wall, the insulating shield sinking thermal energy from within the sample chamber at a second rate $R_2$ slower than the first rate $R_1$; and a liquidus temperature sensor positioned within the sample chamber away from the insulating shield; the method comprising the steps of:

immersing the probe in the molten metal;

flowing the sample of the molten metal into the sample chamber through the passageway until the sample chamber is substantially filled;

sinking thermal energy from and solidifying a portion of the molten metal adjacent the heat sink when the flow ceases, the solidified portion sealing the sample within the sample chamber;

solidifying the sealed sample along a solidification front that progresses toward the insulating shield;

preventing gaseous voids from being formed adjacent the liquidus temperature sensor; and determining from the solidifying sample the liquidus temperature of the molten metal during solidification with the liquidus temperature sensor.

17. The method of claim 16 wherein the probe further comprises a deoxidant within the passageway and wherein the method further comprises the step of deoxidizing the molten metal flowing through the passageway.

18. The method of claim 16 wherein the probe further comprises a bath temperature sensor positioned beyond the immersion face, and wherein the method further comprises the step of concurrently determining a bath temperature of the molten metal with the bath temperature sensor and the liquidus temperature of the molten metal during solidification with the liquidus temperature sensor.

19. The method of claim 18 wherein the probe further comprises a metal cap positioned at the first longitudinal end, the cap covering the bath temperature sensor, and wherein the method further comprises the step of dissolving the metal cap upon contact with the molten metal.

\* \* \* \* \*